US009108987B2

(12) United States Patent
Song et al.

(10) Patent No.: US 9,108,987 B2
(45) Date of Patent: Aug. 18, 2015

(54) SILVER/POLYDIGUANIDE COMPLEX, PREPARATION METHOD THEREOF, AND ANTIBACTERIAL COMPOSITION CONTAINING THE SAME AS AN ACTIVE INGREDIENT

(75) Inventors: Joon Myong Song, Seoul (KR); Sukdeb Pal, Seoul (KR)

(73) Assignee: SNU R&DB Foundation, Seoul (KR)

( * ) Notice: Subject to any disclaimer, the term of this patent is extended or adjusted under 35 U.S.C. 154(b) by 222 days.

(21) Appl. No.: 13/502,337

(22) PCT Filed: Feb. 5, 2010

(86) PCT No.: PCT/KR2010/000717
§ 371 (c)(1),
(2), (4) Date: Apr. 16, 2012

(87) PCT Pub. No.: WO2011/046267
PCT Pub. Date: Apr. 21, 2011

(65) Prior Publication Data
US 2012/0208025 A1    Aug. 16, 2012

(30) Foreign Application Priority Data

Oct. 17, 2009 (KR) .................. 10-2009-0099020
Jan. 7, 2010 (KR) .................. 10-2010-0001428

(51) Int. Cl.
*C07F 1/10* (2006.01)
*C07F 1/00* (2006.01)

(52) U.S. Cl.
CPC ........... *C07F 1/005* (2013.01); *Y10T 428/2982* (2015.01)

(58) Field of Classification Search
None
See application file for complete search history.

(56) References Cited

U.S. PATENT DOCUMENTS

| 4,654,208 | A | 3/1987 | Stockel et al. |
| 2006/0062850 | A1 | 3/2006 | Chen et al. |
| 2009/0123513 | A1 | 5/2009 | Greener |
| 2009/0252861 | A1* | 10/2009 | Tessier et al. ............... 427/2.31 |

OTHER PUBLICATIONS

Pal et al. (Synthesis of Highly Antibacterial Nanocrystalline Trivalent Silver Polydiguanide, Oct. 2009).*
International Search Report prepared by the Korean Intellectual Property Office on Jan. 3, 2011 for International Application No. PCT/KR2010/000717.
Balogh et al., "Dendrimer—Silver Complexes and Nanocomposites as Antimicrobial Agents." Nano Letters. 2001, vol. 1, Issue 1, pp. 18-21.

* cited by examiner

*Primary Examiner* — Ronak Patel
(74) *Attorney, Agent, or Firm* — Sheridan Ross P.C.

(57) ABSTRACT

The present invention relates to a silver/polydiguanide complex and derivatives thereof including silver and polydiguanide having at least two biguanide moieties, wherein the silver is stabilized in an oxidation state of an integer of 0 to 4, a mole ratio between the silver and the polydiguanide is 1:1-4, an average particle diameter of the complex is micrometer or nanometer, and zeta potential of the complex is greater than or equal to zero, a preparation method thereof, and an antibacterial composition for burns or wounds treatment including the same as an active ingredient. A silver/polydiguanide complex according to the present invention is different from conventional silver/polydiguanide complexes in carbon, hydrogen, and nitrogen contents as well as in structure of silver and polydiguanide, and solubility, is a material that exhibits a very good antibacterial activity due to a much lower minimal inhibitory concentration (MIC) value by 10 to 100 folds or more compared to silver sulfadiazine which is a conventional therapeutic agent for burns, and may be usefully used as an antibacterial composition for burns or wounds treatment.

19 Claims, 3 Drawing Sheets

SILVER/POLYDIGUANIDE COMPLEX, PREPARATION METHOD THEREOF, AND ANTIBACTERIAL COMPOSITION CONTAINING THE SAME AS AN ACTIVE INGREDIENT

This application is a national stage application under 35 U.S.C. 371 of PCT Application No. PCT/KR2010/000717, having an international filing date of Feb. 5, 2010, which designated the United States, the entire disclosure of which is hereby incorporated herein by reference. This application claims priority under 35 U.S.C. 119(b) to KR 10-2006-0099020, filed on Oct. 17, 2009, and KR 10-2010-0001428, filed on Jan. 7, 2010, each of which is incorporated by reference in their entirety.

TECHNICAL FIELD

The present invention relates to a silver/polydiguanide complex, a preparation method thereof, and an antibacterial composition containing the same as an active ingredient.

BACKGROUND ART

Metallic silver, silver salts (e.g., $AgNO_3$), and silver complexes have been employed most extensively since ancient times to fight infections and control spoilage in a variety of pharmaceutical and health care applications including anti-infective coatings in medical devices, post-operative wound management and burn wound treatment. Because the metal attacks a broad range of targets in the organisms, microbes are unlikely to develop a resistance against silver, as they do against conventional and highly targeted antibiotics. Indeed, they would have to develop a host of mutations simultaneously to protect themselves. It has been noted that silver ions are responsible for the antibacterial activity. The antibacterial mechanisms of silver may include modifications of sulfur-containing membranes, inhibition of the function of respiratory enzyme(s) facilitating the generation of reactive oxygen species, and inactivation of expression of ribosomal subunit proteins as well as some other cytoplasmic proteins and enzymes essential to ATP production.

Burn wounds, especially large burn wounds, are a critical threat to burn victims, causing dehydration, systemic infection, and other complications. The use of antibacterial agents locally or systemically inhibits microorganism growth around the wound, allowing a suitable microenvironment for healing. The application of silver and its salts in the treatment of burn wounds is thus of special interest, and has prompted an upsurge in research on the synthesis of silver (I) complexes with projected antibacterial application.

There are a variety of inorganic silver-containing antibacterial agents available in practices. For example, U.S. Pat. Nos. 4,911,898 and 4,938,958 disclosed the techniques for carrying sliver zeolite. U.S. Pat. Nos. 5,296,238 and 5,441, 717 disclosed the techniques of silver-containing inorganic zirconium phosphate antibacterial agents, such as $Ag_{0.16}Na_{0.84}Zr_2(PO_4)_3$, $Ag_{0.05}H_{0.05}Na_{0.90}Zr_2(PO_4)_2$ and etc.

Japanese patents 6-263612 and 6-263613 disclosed silver-containing antibacterial agents, such as silver-containing zirconium phosphate, (and silver-containing stannum, phosphate, and silver-containing titanium phosphate), dissolved within the organic solvent to be ground by zirconia spheres under a dispersant agent so as to increase its antibacterial activity. JP2000-68914 disclosed the use of applying acetic acid into inorganic antibacterial agents to increase its antibacterial performance. These antibacterial agents described above are essentially monovalent silver antibacterial agents.

However, such antibacterial agents containing monovalent silver known in prior art are not pharmaceutically acceptable especially for burn and wound care treatment. N-heterocyclic carbene silver (I) complexes have good antibacterial property, but decompose in aqueous solutions. Therefore, for better exploitation of silver-based antibacterial therapies in medicine it is necessary to develop new pharmaceutically acceptable and stable silver complexes.

Even though antibacterial agents containing monovalent silver demonstrate good antibacterial efficacy, monovalent silver is very photosensitive. Upon exposure to electromagnetic radiation it undergoes discoloration. The antibacterial performance of silver ion is correlated to its valence form and although antibacterial performance of the different silver valence varies in treating heterogeneous bacteria, it is generally known that high valence silver ions exhibit stronger and more effective antibacterial action than low valence ions.

It is widely known that divalent silver has higher antibacterial performance than monovalent silver. US Pat. Appl. No. 20070042052 disclosed antibacterial agents containing divalent silver. However, such divalent sliver will be only kept stable in concentrated acidic environment. As a result, it would be rather difficult and dangerous for the operation, usage, and transportation of such agents. U.S. Pat. No. 5,089, 275 disclosed a type of solid antibacterial compound containing divalent silver. This compound is prepared by reacting an acidic fluid divalent silver complex with anhydrous calcium sulfate so as to obtain a stable hydrated solid.

Although the solid antibacterial agents containing divalent silver solves the issue of the liquid state of divalent silver antibacterial agents, the product still faces the deficiency of long term storage stability in solid state. Therefore, the field of application is limited due to the fact to its water solubility. i.e. such solid antibacterial agents have to be used in cleaning water, such as swimming pool, bathtub, industry cooling system, and so on.

Encouraging results have recently been reported regarding the bactericidal activity of silver nanoparticles of either simple or composite nature. The high surface to volume ratio of nanoparticles ensures that a significantly large surface area of the particle is in contact with the bacteria. Smaller particle size silver sulfadiazine product demonstrates increased antibacterial effectiveness and these smaller particles are better stabilized by adsorbed surfactant.

Encouraged by this finding and by the pressing interest in developing silver-containing antibacterial agents with excellent optical stability and antibacterial activity, the present inventors have found that a silver/polydiguanide complex of the present invention is different from conventional silver/polydiguanide complexes in carbon, hydrogen, and nitrogen contents as well as in structure of silver and polydiguanide, and solubility, is a material that exhibits a very good antibacterial activity due to a much lower minimal inhibitory concentration (MIC) value by 10 to 100 folds or more compared to silver sulfadiazine which is a conventional therapeutic agent for burns, and may be usefully used as an antibacterial composition for burns or wounds treatment, leading to completion of the present invention.

DISCLOSURE OF INVENTION

Technical Problem

A primary object of the present invention is to provide a microcrystalline silver/polydiguanide complex or pharmaceutically acceptable derivatives thereof and a preparation method thereof.

Another object of the present invention is to provide a nanocrystalline silver/polydiguanide complex or pharmaceutically acceptable derivatives thereof and a preparation method thereof.

Yet another object of the present invention is to provide an antibacterial composition for burns or wounds treatment, containing the microcrystalline silver/polydiguanide complex or nanocrystalline silver/polydiguanide complex or pharmaceutically acceptable derivatives thereof as an active ingredient.

Solution to Problem

To achieve the above objects, the present invention provides a microcrystalline silver/polydiguanide complex or pharmaceutically acceptable derivatives thereof including silver and polydiguanide having at least two biguanide moieties, wherein the silver is stabilized in an oxidation state of an integer of 0 to 4, a mole ratio between the silver and the polydiguanide is 1:1-4, an average particle diameter of the complex is ranged from 0.2 μm to 1000 μm, and zeta potential of the complex is greater than or equal to zero.

The present invention also provides a method for preparing the microcrystalline silver/polydiguanide complex.

Furthermore, the present invention provides a nanocrystalline silver/polydiguanide complex or pharmaceutically acceptable derivatives thereof including silver and polydiguanide having at least two biguanide moieties, wherein the silver is stabilized in an oxidation state of an integer of 0 to 4, a mole ratio between the silver and the polydiguanide is 1:1-4, an average particle diameter of the complex is ranged from 1 nm to 200 nm, and zeta potential of the complex is greater than or equal to zero.

The present invention also provides a method for preparing the nanocrystalline silver/polydiguanide complex.

Furthermore, the present invention provides an antibacterial composition for burns or wounds treatment, containing the microcrystalline silver/polydiguanide complex or nanocrystalline silver/polydiguanide complex or pharmaceutically acceptable derivatives thereof as an active ingredient.

Advantageous Effects of Invention

A silver/polydiguanide complex according to the present invention is different from conventional silver/polydiguanide complexes in carbon, hydrogen, and nitrogen contents as well as in structure of silver and polydiguanide, and solubility, is a material that exhibits a very good antibacterial activity due to a much lower minimal inhibitory concentration (MIC) value by 10 to 100 folds or more compared to silver sulfadiazine which is a conventional therapeutic agent for burns, and may be usefully used as an antibacterial composition for burns or wounds treatment.

BEST MODE FOR CARRYING OUT THE INVENTION

The present invention provides a microcrystalline silver/polydiguanide complex or pharmaceutically acceptable derivatives thereof including silver and polydiguanide having at least two biguanide moieties, wherein the silver is stabilized in an oxidation state of an integer of 0 to 4, a mole ratio between the silver and the polydiguanide is 1:1-4, an average particle diameter of the complex is ranged from 0.2 μm to 1000 μm, and zeta potential of the complex is greater than or equal to zero.

Hereinafter, the present invention will be described in detail.

The silver is stabilized in an oxidation state of an integer of 0 to 4, and silver acetate, silver acetylacetonate, silver benzoate, silver bromide, silver carbonate, silver chloride, silver citrate, silver cyanate, silver cyclohexanebutyrate, silver fluoride, silver iodide, silver lactate, silver methanesulfonate, silver nitrate, silver perchlorate, silver permanganate, silver phosphate, silver sulfadiazine, silver sulphate, silver tetrafluoroborate, silver thiocyanate, silver p-tolunesulfonate, silver trifluoroacetate, silver trifluoromethanesulphonate, etc. may be used as a source for the silver.

The polydiguanide has at least two biguanide moieties. Poly(hexamethylenebiguanide), chlorhexidine (1,1'-hexamethylenebis[5-(p-chlorphenyl)biguanide]), metformin (N',N'-dimethylbiguanide), phenformin (phenethylbiguanide), buformin (N-butylbiguanide), etc. may be used as a source for the polydiguanide, and chlorhexidine (1,1'-hexamethylenebis[5-(p-chlorphenyl) biguanide]) is preferably used.

In the microcrystalline silver/polydiguanide complex according to the present invention, a mole ratio between the silver and the polydiguanide is preferably 1:1-4, and more preferably 1:1-2.

The present invention also provides a method for preparing a microcrystalline silver/polydiguanide complex.

Preparation Method #1: Preparation of a Microcrystalline Silver (I)/Polydiguanide Complex A microcrystalline silver (I)/polydiguanide complex according to the present invention may be prepared by a preparation method, including:

preparing an aqueous solution of polydiguanide by adjusting the pH (Step 1);

adding an aqueous solution containing silver (I) into the aqueous solution of polydiguanide obtained in Step 1, followed by stirring to obtain a homogeneous reaction mixture (Step 2);

precipitating a microcrystalline silver (I)/polydiguanide complex by adjusting the pH of the reaction mixture obtained in Step 2 (Step 3); and filtering and drying the microcrystalline silver (I)/polydiguanide complex precipitated in Step 3 to ultimately obtain the complex (Step 4).

Hereinafter, the preparation method #1 according to the present invention will be described in more detail step by step.

First, Step 1 according to the present invention is a step in which the pH is adjusted to prepare an aqueous solution of polydiguanide. The polydiguanide may be solubilized in an acidic solution to prepare an aqueous solution of polydiguanide. Then, the pH is adjusted preferably to a range of 0 to 3, more preferably to a range of 1 to 2 in order to prepare the acidic solution. Sulfuric acid, nitric acid, perchloric acid, etc. may be used to adjust the pH.

Next, Step 2 is a step in which an aqueous solution containing silver (I) is added into the aqueous solution of polydiguanide obtained in Step 1, followed by stirring to obtain a homogeneous reaction mixture.

Subsequently, Step 3 is a step in which the pH of the reaction mixture obtained in Step 2 is adjusted to precipitate a microcrystalline silver (I)/polydiguanide complex. The microcrystalline silver (I)/polydiguanide complex may be precipitated by increasing the pH of the acidic reaction mixture. Then, the pH of the acidic reaction mixture is adjusted preferably to a range of 3 to 8, more preferably to a range of 6 to 7.5. Sodium hydroxide, potassium hydroxide, sodium carbonate, sodium bicarbonate, potassium carbonate, etc. may be used to adjust the pH.

Next, Step 4 is a step in which the microcrystalline silver (I)/polydiguanide complex precipitated in Step 3 is filtered and dried. The filtration further may comprise sub-steps for washing a filter cake with water, methanol or a mixture thereof. The filter cake is dried preferably at 0° C. to 100° C., more preferably at 20° C. to 30° C.

Preparation Method #2: Preparation of a Microcrystalline Silver (I)/Polydiguanide Complex A microcrystalline silver (I)/polydiguanide according to the present invention may be prepared by a preparation method, including:

solubilizing polydiguanide in an organic solvent to prepare a polydiguanide solution (Step 1);

adding an aqueous solution containing silver (I) into the polydiguanide solution obtained in Step 1, followed by stirring to obtain a homogeneous reaction mixture (Step 2);

precipitating the microcrystalline silver (I)/polydiguanide complex by lowering the temperature of the reaction mixture obtained in Step 2 (Step 3); and filtering and drying the microcrystalline silver (I)/polydiguanide complex precipitated in Step 3 to ultimately obtain the complex (Step 4).

Hereinafter, the preparation method #2 according to the present invention will be described in more detail step by step.

First, Step 1 according to the present invention is a step in which polydiguanide is solubilized in an organic solvent to prepare a polydiguanide solution, and methanol or DMSO is preferably used as the organic solvent.

Next, Step 2 is a step in which an aqueous solution containing silver (I) is added into the polydiguanide solution obtained in Step 1, followed by stirring to obtain a homogeneous reaction mixture.

Subsequently, Step 3 is a step in which the temperature of the reaction mixture obtained in Step 2 is lowered to precipitate the microcrystalline silver (I)/polydiguanide complex.

By the preparation method according to the present invention, polydiguanide may be solubilized in an organic solvent such as warm methanol or DMSO at room temperature, into which solution an aqueous solution containing silver is added and stirred to homogenize the reaction mixture. The temperature may be lowered to precipitate and obtain a microcrystalline silver/polydiguanide complex.

Next, Step 4 is a step in which the microcrystalline silver (I)/polydiguanide complex precipitated in Step 3 is filtered and dried. The filtration further may comprise sub-steps for washing a filter cake with water, methanol or a mixture thereof. The filter cake is dried preferably at 0° C. to 100° C., more preferably at 20° C. to 30° C.

Preparation Method #3: Preparation of a Microcrystalline Silver (II-IV)/Polydiguanide Complex A microcrystalline silver (II-IV)/polydiguanide complex according to the present invention may be prepared by a preparation method, including:

preparing an aqueous solution of polydiguanide by adjusting the pH (Step 1);

adding an aqueous solution containing silver (I) into the aqueous solution of polydiguanide obtained in Step 1, followed by stirring to obtain a homogeneous reaction mixture (Step 2);

oxidizing the silver (I) to a high valent silver by adding an oxidizing agent into the reaction mixture obtained in Step 2 (Step 3);

precipitating a microcrystalline silver (II-IV)/polydiguanide complex by adjusting the pH of the reaction mixture obtained in Step 3 (Step 4); and filtering and drying the microcrystalline silver (II-IV)/polydiguanide complex precipitated in Step 4 to ultimately obtain the complex (Step 5).

Hereinafter, the preparation method #3 according to the present invention will be described in more detail step by step.

First, Step 1 according to the present invention is a step in which the pH is adjusted to prepare an aqueous solution of polydiguanide. The polydiguanide may be solubilized in an acidic solution to prepare an aqueous solution of polydiguanide. Then, the pH is adjusted preferably to a range of 0 to 3, more preferably to a range of 1 to 2 in order to prepare the acidic solution. Sulfuric acid, nitric acid, perchloric acid, etc. may be used to adjust the pH.

Next, Step 2 is a step in which an aqueous solution containing silver (I) is added into the aqueous solution of polydiguanide obtained in Step 1, followed by stirring to obtain a homogeneous reaction mixture.

Subsequently, Step 3 is a step in which the silver in the reaction mixture obtained in Step 2 is oxidized to a high valent silver by adding an oxidizing agent. The oxidizing agent may be any one selected from a group consisting of sodium peroxydisulfate, potassium peroxydisulfate, ammonium peroxydisulfate, and red lead, or any mixture thereof. The oxidation in Step 3 may be achieved by adding the oxidizing agent at a predetermined condition, wherein a pH value is ranged from 1 to 5, temperature is ranged from 0° C. to 80° C., reacting time is ranged from 30 seconds to 8 hours, preferably a pH value is ranged from 1 to 3, temperature is ranged from 20° C. to 30° C., reacting time is ranged from 5 minutes to 1 hours, Next, Step 4 is a step in which the pH of the reaction mixture obtained in Step 3 is adjusted to precipitate a microcrystalline silver (II-IV)/polydiguanide complex. The microcrystalline silver (II-IV)/polydiguanide complex may be precipitated by increasing the pH of the acidic reaction mixture obtained in Step 2. Then, the pH of the acidic reaction mixture is adjusted preferably to a range of 3 to 8, more preferably to a range of 6 to 7.5. Sodium hydroxide, potassium hydroxide, sodium carbonate, sodium bicarbonate, potassium carbonate, etc. may be used to adjust the pH.

Next, Step 5 is a step in which the microcrystalline silver (II-IV)/polydiguanide complex precipitated in Step 4 is filtered and dried. The filtration further may comprise sub-steps for washing a filter cake with water, methanol or a mixture thereof. The filter cake is dried preferably at 0° C. to 100° C., more preferably at 20° C. to 30° C.

By a citrate reduction generally known in the art, a microcrystalline silver/polydiguanide complex prepared according to the method may be reduced to one stabilized in an oxidation state of zero. The citrate reduction is used as a method for preparing gold or silver colloidal particles, and sodium citrate ($Na_3C_6H_5O_7$) is used as a reducing agent.

Furthermore, the present invention provides a nanocrystalline silver/polydiguanide complex or pharmaceutically acceptable derivatives thereof including silver and polydiguanide having at least two biguanide moieties, wherein the silver is stabilized in an oxidation state of an integer of 0 to 4, a mole ratio between the silver and the polydiguanide is 1:1-4, an average particle diameter of the complex is ranged from 1 nm to 200 nm, and zeta potential of the complex is greater than or equal to zero.

The silver is stabilized in an oxidation state of an integer of 0 to 4, and silver acetate, silver acetylacetonate, silver benzoate, silver bromide, silver carbonate, silver chloride, silver citrate, silver cyanate, silver cyclohexanebutyrate, silver fluoride, silver iodide, silver lactate, silver methanesulfonate, silver nitrate, silver perchlorate, silver permanganate, silver phosphate, silver sulfadiazine, silver sulphate, silver tetrafluoroborate, silver thiocyanate, silver p-tolunesulfonate, silver trifluoroacetate, silver trifluoromethanesulphonate, etc. may be used as a source for the silver.

The polydiguanide has at least two biguanide moieties. Poly(hexamethylenebiguanide), chlorhexidine (1,1'-hexamethylenebis[5-(p-chlorphenyl) biguanide]), metformin (N', N'-dimethylbiguanide), phenformin (phenethylbiguanide), buformin (N-butylbiguanide), etc. may be used as a source for the polydiguanide, and chlorhexidine (1,1'-hexamethylenebis[5-(p-chlorphenyl) biguanide]) is preferably used.

In the nanocrystalline silver/polydiguanide complex according to the present invention, a mole ratio between the silver and the polydiguanide is preferably 1:1-4, and more preferably 1:1-2.

The present invention also provides a method for preparing a nanocrystalline silver/polydiguanide complex.

Preparation Method A: Preparation of a Nanocrystalline Silver (I)/Polydiguanide Complex A nanocrystalline silver (I)/polydiguanide complex may be prepared by a preparation method, including:

preparing a water-in-oil (W/O) microemulsion or reverse microemulsion (Step 1);

adding an aqueous solution of polydiguanide into the water-in-oil (W/O) microemulsion or reverse microemulsion prepared in Step 1 (Step 2);

adding an aqueous solution containing silver (I) into the resultant solution in Step 2 to prepare a reaction mixture (Step 3); and precipitating a nanocrystalline silver (I)/polydiguanide complex by adjusting the pH of the reaction mixture in Step 3 (Step 4).

Hereinafter, the preparation method A according to the present invention will be described in more detail step by step.

First, Step 1 according to the present invention is a step in which a water-in-oil (W/O) microemulsion or reverse microemulsion is prepared. The water-in-oil (W/O) microemulsion or reverse microemulsion composition may lie anywhere in the phase diagram of the ternary system of a water/surfactant/organic solvent that represents a region where the ternary system forms a thermodynamically stable microemulsion. The water-in-oil (W/O) microemulsion or reverse microemulsion may contain any cationic, anionic, zwiterionic, nonionic surfactant dissolved in an oil which is an organic solvent, or organic solvent. The water-in-oil (W/O) microemulsion or reverse microemulsion may additionally contain a co-surfactant which is a cationic, anionic, zwiterionic or non-ionic surfactant or an organic solvent.

The water-in-oil (W/O) microemulsion or reverse microemulsion may be prepared by solubilizing a surfactant in an organic solvent, followed by stirring. Then, an ultrasonic bath may be used to reach a finer and more stable state of the microemulsion or reverse microemulsion.

Next, Step 2 is a step in which an aqueous solution of polydiguanide is added into the water-in-oil (W/O) microemulsion or reverse microemulsion prepared in Step 1, preferably added drop wise. The polydiguanide may be solubilized in an acidic solution to prepare the aqueous solution of polydiguanide. Then, the pH is adjusted preferably to a range of 0 to 3, more preferably to a range of 1 to 2 in order to prepare the acidic solution. Sulfuric acid, nitric acid, perchloric acid, etc. may be used to adjust the pH.

Subsequently, Step 3 is a step in which an aqueous solution containing silver (I) is added to prepare a reaction mixture, and the aqueous solution containing silver (I) is preferably added drop wise.

Next, Step 4 is a step in which a nanocrystalline silver (I)/polydiguanide complex is precipitated by adjusting the pH of the reaction mixture in Step 3. The nanocrystalline silver (I)/polydiguanide complex may be precipitated by increasing the pH of the acidic reaction mixture obtained in Step 3. Then, the pH of the acidic reaction mixture is adjusted preferably to a range of 3 to 8, more preferably to a range of 6 to 7.5. Sodium hydroxide, potassium hydroxide, sodium carbonate, sodium bicarbonate, potassium carbonate, etc. may be used to adjust the pH.

Preparation Method B: Preparation of a Nanocrystalline Silver (II-IV)/Polydiguanide Complex A nanocrystalline silver (II-IV)/polydiguanide complex according to the present invention may be prepared by a preparation method, including:

preparing a water-in-oil (W/O) microemulsion or reverse microemulsion (Step 1);

adding an aqueous solution of polydiguanide into the water-in-oil (W/O) microemulsion or reverse microemulsion prepared in Step 1 (Step 2);

adding an aqueous solution containing silver (I) into the resultant solution in Step 2 to prepare a reaction mixture (Step 3);

oxidizing the silver (I) to a high valent silver by adding an oxidizing agent into the reaction mixture obtained in Step 3 (Step 4);

precipitating a nanocrystalline silver (II-IV)/polydiguanide complex by adjusting the pH of the reaction mixture in Step 4 (Step 5).

Hereinafter, the preparation method B according to the present invention will be described in more detail step by step.

First, Step 1 according to the present invention is a step in which a water-in-oil (W/O) microemulsion or reverse microemulsion is prepared. The water-in-oil (W/O) microemulsion or reverse microemulsion composition may lie anywhere in the phase diagram of the ternary system of a water/surfactant/organic solvent that represents a region where the ternary system forms a thermodynamically stable microemulsion. The water-in-oil (W/O) microemulsion or reverse microemulsion may contain any cationic, anionic, zwiterionic, nonionic surfactant dissolved in an oil which is an organic solvent, or organic solvent. The water-in-oil (W/O) microemulsion or reverse microemulsion may additionally contain a co-surfactant which is a cationic, anionic, zwiterionic or non-ionic surfactant or an organic solvent.

The water-in-oil (W/O) microemulsion or reverse microemulsion may be prepared by solubilizing a surfactant in an organic solvent, followed by stirring. Then, an ultrasonic bath may be used to reach a finer and more stable state of the microemulsion or reverse microemulsion.

Next, Step 2 is a step in which an aqueous solution of polydiguanide is added into the water-in-oil (W/O) microemulsion or reverse microemulsion prepared in Step 1, preferably added drop wise. The polydiguanide may be solubilized in an acidic solution to prepare the aqueous solution of polydiguanide. Then, the pH is adjusted preferably to a range of 0 to 3, more preferably to a range of 1 to 2 in order to prepare the acidic solution. Sulfuric acid, nitric acid, perchloric acid, etc. may be used to adjust the pH.

Subsequently, Step 3 is a step in which an aqueous solution containing silver (I) is added into the resultant solution in Step 2 to prepare a reaction mixture, and the aqueous solution containing silver (I) is preferably added drop wise.

Next, Step 4 is a step in which the silver in the reaction mixture obtained in Step 3 is oxidized to a high valent silver by adding an oxidizing agent. The oxidizing agent may be any one selected from a group consisting of sodium peroxydisulfate, potassium peroxydisulfate, ammonium peroxydisulfate, and red lead, or any mixture thereof. The oxidation in Step 4 may be achieved by adding the oxidizing agent at a predetermined condition, wherein a pH value is ranged from 1 to 5, temperature is ranged from 0° C. to 80° C., reacting time is ranged from 30 seconds to 8 hours, preferably a pH value is ranged from 1 to 3, temperature is ranged from 20° C. to 30° C., reacting time is ranged from 5 minutes to 1 hours, Subsequently, Step 5 is a step in which a nanocrystalline silver (II-IV)/polydiguanide complex is precipitated by adjusting the pH of the reaction mixture in Step 4. The nanocrystalline silver (II-IV)/polydiguanide complex may be precipitated by increasing the pH of the acidic reaction mixture obtained in Step 4. Then, the pH of the acidic reaction mixture is adjusted preferably to a range of 3 to 8, more preferably to a range of 6 to 7.5. Sodium hydroxide, potassium hydroxide, sodium carbonate, sodium bicarbonate, potassium carbonate, etc. may be used to adjust the pH.

By a citrate reduction generally known in the art, a nanocrystalline silver/polydiguanide complex prepared by the preparation method may be reduced to one stabilized in an oxidation state of zero. The citrate reduction is used as a method for preparing gold or silver colloidal particles, and sodium citrate ($Na_3C_6H_5O_7$) is used as a reducing agent.

Furthermore, the present invention provides an antibacterial composition for burns or wounds treatment containing a microcrystalline silver/polydiguanide complex or mixtures thereof as an active ingredient, wherein the silver is stabilized in an oxidation state of an integer of 0 to 4.

The present invention also provides an antibacterial composition for burns or wounds treatment containing a nanocrystalline silver/polydiguanide complex or mixtures thereof as an active ingredient, wherein the silver is stabilized in an oxidation state of an integer of 0 to 4.

The antibacterial composition for burns or wounds treatment is used for antibacterial purposes, is not specifically limited to the formulation, and may additionally contain at least one active ingredient having the same or similar function to the silver/polydiguanide complex.

The composition may be for external application, specifically in the form of solution, suspension, spray, patch, pad, cream, ointment, and gel. The solution may contain, in addition to the active compound, conventional excipients, for example solvents, solubilizing agents, and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, camellia oil, aloe vera, glycerin, natural maize germ oil, olive oil, castor oil, almond oil and sesame oil, glycerol, glycerol form alcohol, tetrahydrofurfuryl alcohol, polyethylene glycols and fatty acid esters of sorbitan, or mixtures of these substances, and preservatives such as methyl or propyl-p-hydroxybenzoate or sorbic acid.

The suspension may contain, in addition to the active compound, conventional excipients, for example liquid diluents (for example: water, ethyl alcohol, propylene glycol, and polyethylene glycol), and suspending agents (for example: ethoxylated isostearyl alcohols, polyoxyethylene sorbitol, sorbitan esters, cellulose derivatives, and hydrogenated vegetable oils), microcrystalline cellulose, aluminum metahydroxide, bentonite, agar-agar and tragacanth, injectable ester such as ethyl oleate, or mixtures of these substances.

The ointment, cream, and gel may contain, in addition to the active compound, conventional excipients, for example animal and vegetable fats, wax paraffins, starch, tragacanth, cellulose derivatives, polyethylene glycols, silicones, bentonites, silicic acid, talc and zinc oxide, or mixtures of these substances.

The composition may be employed in antibacterial clothing, antibacterial daily products, antibacterial plastic products, antibacterial medical and mechanical devices, antibacterial structure materials, antibacterial ceramics, antibacterial sanitary ware, antibacterial home electronic appliances, etc.

MODE FOR THE INVENTION

Hereinafter, the present invention will be described in detail with reference to embodiments. However, the following embodiments are provided only to illustrate the present invention, and the present invention is not limited to them.

Example 1

Preparation of a Microcrystalline Silver (I)/Chlorhexidine Complex 1

Step 1 of Preparation #1: Preparation of a Chlorhexidine Aqueous Solution 0.49 mmol of chlorhexidine (1,1'-hexamethylenebis[5-p-chlorphenyl]biguanide) (0.25 g) was dissolved in 25 ml dilute sulphuric acid (2N) and stirred to prepare a chlorhexidine aqueous solution.

Step 2 of Preparation #1: Addition of an Aqueous Solution Containing Silver (I)

To the chlorhexidine aqueous solution prepared in Step 1 of Preparation #1 was added drop wise an aqueous solution (1.25 ml) containing 0.05 mmol of silver nitrate (0.085 g).

Step 3 of Preparation #1: Precipitation of a Microcrystalline Silver (I)/Polydiguanide Complex The pH of the reaction mixture was subsequently adjusted to 7.0 by drop wise addition of a saturated aqueous solution of sodium bicarbonate into a reaction mixture of silver (I)/chlorhexidine prepared in Step 2. The reaction mixture was allowed to remain under stirring condition for at least 10 minutes and stand for at least 4 hours at room temperature to yield a white precipitate of a microcrystalline silver (I)/polydiguanide complex.

Step 4 of Preparation #1: Filterin and Drying of a Microcrystalline Silver (I)/Polydiguanide Complex The white precipitate of the microcrystalline silver (I)/polydiguanide complex obtained in Step 3 was filtered under vacuum, washed with water, and dried at ambient temperature to finally yield a microcrystalline silver (I)/polydiguanide complex.

Example 2

Preparation of a Microcrystalline Silver (II)/Chlorhexidine Complex 1

Step 1 of Preparation #3: Preparation of a Chlorhexidine Aqueous Solution 0.49 mmol of chlorhexidine (1,1'-hexamethylenebis[5-p-chlorphenyl]biguanide) (0.25 g) was dissolved in 25 ml dilute sulphuric acid (2N) and stirred to prepare a chlorhexidine aqueous solution.

Step 2 of Preparation #3: Addition of an Aqueous Solution Containing Silver (I)

To the chlorhexidine solution prepared in Step 1 of Preparation #3 was added drop wise an aqueous solution (1.25 ml) containing 0.05 mmol of silver nitrate (0.085 g).

Step 3 of Preparation #3: Addition of an Oxidizing Agent

To a reaction mixture of silver (I) and chlorhexidine prepared in Step 2 of Preparation #3 was added an aqueous solution (1.25 ml) containing 0.99 mmol of sodium persulphate (0.235 g) as an oxidizing agent.

Step 4 of Preparation #3: Preparation of a Microcrystalline Silver (II)/Polydiguanide Complex To a reaction mixture of silver (II) and chlorhexidine prepared in Step 3 of Preparation #3 was added drop wise a saturated aqueous solution of sodium bicarbonate to adjust the pH of the reaction mixture to 7.0. The reaction mixture was allowed to remain under stirring condition for at least 10 minutes and stand for at least 4 hours at room temperature to yield a brown precipitate of a microcrystalline silver (II)/polydiguanide complex.

Step 5 of Preparation #3: Filtering and Drying of a Microcrystalline Silver (I)/Polydiguanide Complex The brown precipitate of the microcrystalline silver (II)/polydiguanide complex obtained in Step 4 was filtered under vacuum, washed with water, and dried at ambient temperature to finally yield a microcrystalline silver (II)/polydiguanide complex.

Example 3

Preparation of a Microcrystalline Silver (II)/Chlorhexidine Complex 2

A microcrystalline silver (II)/chlorhexidine complex was obtained in the same way as in Example 2 except that nitric acid was used instead of the sulfuric acid in Step 1 in Example 2.

Example 4

Preparation of a Nanocrystalline Silver (III)/Chlorhexidine Complex 1

Step 1 of Preparation B: Preparation of a Water-In-Oil (W/O) Microemulsion

A W/O microemulsion was established by dissolving dioctyl sulfosuccinate (AOT, 0.1 M) as a surfactant in heptane (10 ml).

Step 2 of Preparation B: Addition of a Chlorhexidine Aqueous Solution 0.49 mmol of chlorhexidine (1,1'-hexamethylenebis[5-p-chlorphenyl]biguanide) (0.25 g) was dissolved in 25 ml dilute sulphuric acid (2N) and stirred to prepare a chlorhexidine aqueous solution. To the W/O microemulsion prepared in Step 1 was added drop wise the chlorhexidine aqueous solution.

Step 3 of Preparation B: Addition of an Aqueous Solution Containing Silver (I)

To the W/O microemulsion prepared in Step 2 was added drop wise an aqueous solution (1.25 ml) containing 0.05 mmol of silver nitrate (0.085 g).

Step 4 of Preparation B: Addition of an Oxidizing Agent

To the W/O microemulsion prepared in Step 3 was added drop wise an aqueous solution (1.25 ml) containing 0.99 mmol of sodium persulphate (0.235 g) as an oxidizing agent.

Step 5 in Preparation B: Precipitation of a Nanocrystalline Silver (III)/Polydiguanide Complex To the W/O microemulsion prepared in Step 4 was added drop wise a saturated aqueous solution of sodium bicarbonate to adjust the pH of the reaction mixture to 7.0, yielding a precipitate of a nanocrystalline silver (III)/polydiguanide complex.

Comparative Example 1

Preparation of a Microcrystalline Silver (III)/Chlorhexidine Complex

According to a method described in WO2007/000590, a microcrystalline silver (III)/chlorhexidine complex was prepared. 0.49 mmol of chlorhexidine (1,1'-hexamethylenebis[5-p-chlorphenyl]biguanide) (0.25 g) was dissolved in 25 ml warm methanol and stirred to prepare a chlorhexidine solution. To the chlorhexidine solution was added drop wise an aqueous solution (1.25 ml) containing 0.05 mmol of silver nitrate (0.085 g). To the reaction mixture of silver (I) and chlorhexidine was added drop wise an aqueous solution (1.25 ml) containing 0.99 mmol of sodium persulphate (0.235 g) as oxidizing agent. After the addition of an oxidizing agent, the reaction mixture was warmed until an orange-brown is fully developed. The precipitate was filtered under vacuum and washed three times with warm methanol to yield a microcrystalline silver (III)/chlorhexidine complex.

Experimental Example 1

Measurement of Chemical Properties

To measure chemical properties of a silver/polydiguanide complex according to the present invention, the following experiments were performed.

1. Elemental Analysis

Elemental analyses were performed on Examples 1 to 3 according to the present invention and Comparative Example 1.

CHN analysis is the most commonly used analysis for determination of carbon, hydrogen, and nitrogen contents of sample. The sample is burnt in presence of pure oxygen, and as a result, carbon dioxide, water, and nitrogen dioxide produced in the process are collected. The mass of the oxidized materials may be used to estimate the composition of an unknown sample. A synthesized sample was placed into a capsule and burnt, and an EA 1110 CHNS-O (CE INSTRUMENT) was used to determine its C,H, and N contents.

The results are summarized in the following Table 1.

TABLE 1

|  | C (%) | H (%) | N (%) |
|---|---|---|---|
| Example 1 | 37.90 | 4.59 | 19.89 |
| Example 2 | 39.31 | 4.77 | 20.87 |

TABLE 1-continued

|  | C (%) | H (%) | N (%) |
|---|---|---|---|
| Example 3 | 38.83 | 4.76 | 22.31 |
| Comparative Example 1 | 16.55 | 1.84 | 8.70 |

Referring to Table 1, it can be seen that Examples 1 to 3 according to the present invention had higher carbon, hydrogen, and nitrogen contents than Comparative Example 1.

Therefore, a silver/polydiguanide complex according to the present invention is a material different from conventional silver/polydiguanide complexes because the complex according to the present invention is different from conventional silver/polydiguanide complexes in carbon, hydrogen, and nitrogen contents.

2. Mass Analysis

Mass analyses were performed on Example 4 according to the present invention and Comparative Example 1. The mass analysis method was performed as follows. A sample solution was injected and flowed into a thin capillary tube into which a high electric potential was applied. When the solution was flown out of the end of the capillary tube, the solution generated a mist of lots of charged ion droplets due to an electric effect by a high electric potential. When an electrostatic force resulting from accumulated cations increases more than the surface tension of the droplets, the ion droplets are introduced into a mass spectrometer inlet port by the gradients of electric and pressure fields while the solvents in the ion droplets were evaporated. Through a secondary dissociation resulting from the evaporation, the droplets were turned into smaller droplets, ultimately leaving behind only unimolecular ions. The synthesized sample was dissolved in dimethylsulfoxide, followed by injection into an Ion Trap Mass LCQ (Finnigan MAT, U.S.A) through a syringe for analysis.

Figure 1:
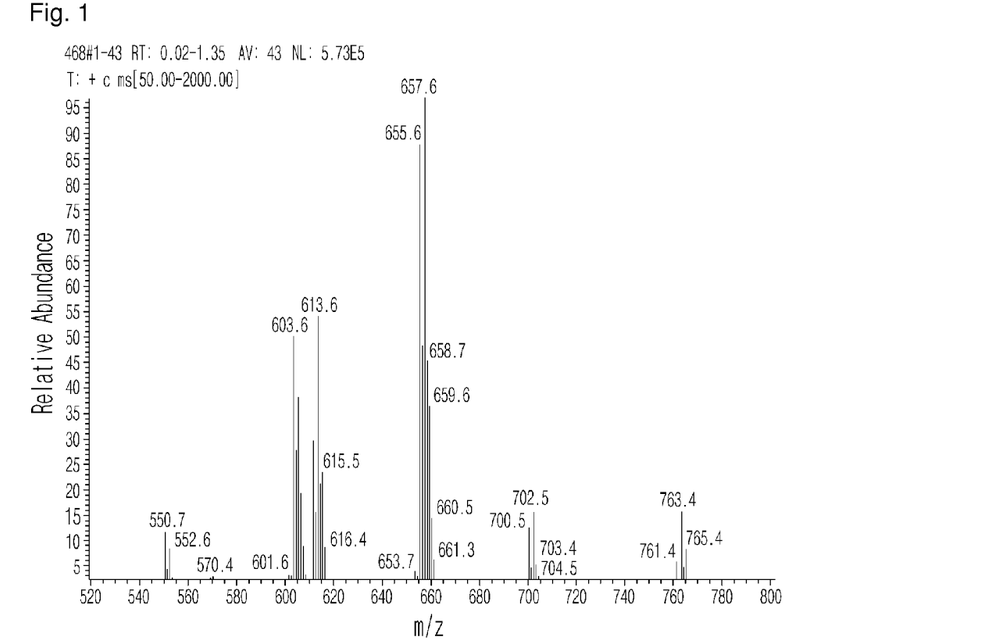
FIG. 1 is an ESI-MS spectrum of Example 4 according to the present invention.
Figure 2:
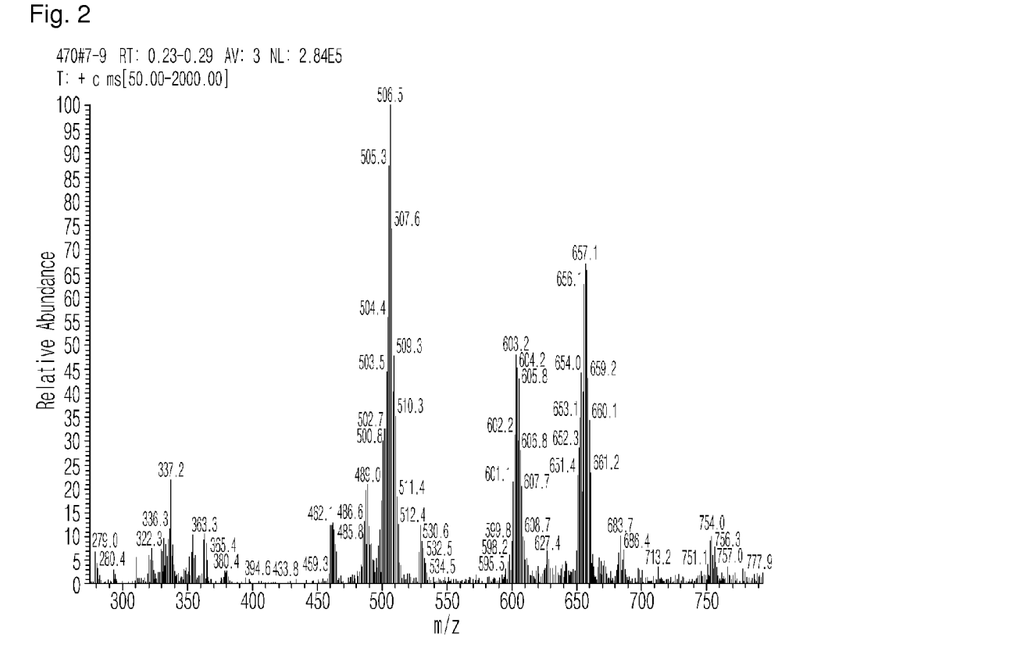
FIG. 2 is an ESI-MS spectrum of Comparative Example 1 according to the present invention.

The results are illustrated in FIGS. 1 and 2. More specifically, ESI-MS spectra of Example 4 according to the present invention and Comparative Example 1 are shown in FIG. 1 and FIG. 2, respectively.

As illustrated in FIG. 1, it can be seen that a silver/polydiguanide complex in Example 4 according to the present invention has a molecular weight peak at 613 when the ratio of silver to chlorhexidine is 1:1.

As illustrated in FIG. 2, it can be seen that a silver/polydiguanide complex in Comparative Example 1 is different from a silver/polydiguanide complex in Example 4 in spectrum, and has no molecular weight peak at 613 when the ratio of silver to chlorhexidine is 1:1.

Therefore, a silver/polydiguanide complex according to the present invention is a material different from conventional silver/polydiguanide complexes because the complex according to the present invention is different from conventional silver/polydiguanide complexes in structures of silver and polydiguanide.

3. Measurement of Solubility

Solubilities of samples in Example 2 according to the present invention and in Comparative Example 1 in DMSO were measured. DMSO was added into each of 2 mg of samples in Example 2 and Comparative Example 1 until each of them is completely dissolved, and the amount of DMSO added was measured.

As a result, 53 ml and 800 µl of DMSO were used to dissolve each of 2 mg of samples in Example 2 and Comparative Example 1, respectively. It can be seen that the degree of dissolution of a sample in Example 2 according to the present invention is lower than that of a sample in Comparative Example 1 by about 66.25 folds.

Therefore, a silver/polydiguanide complex according to the present invention is a material different from conventional silver/polydiguanide complexes because the complex according to the present invention has a solubility value different from those of conventional silver/polydiguanide complexes.

From these results, a silver/polydiguanide complex according to the present invention is different from conventional silver/polydiguanide complexes because the complex according to the present invention is different from conventional silver/polydiguanide complexes in carbon, hydrogen, and nitrogen contents as well as in structure of silver and polydiguanide, and those complexes has different solubility values.

Experimental Example 2

Measurement of Oxidation State of Silver

To measure the oxidation state of silver in a silver/polydiguanide complex according to the present invention, the following experiment was performed.

The oxidation states of samples in Examples 1, 2, and 4 according to the present invention were each measured by X-ray photoelectron spectroscopy (XPS). When an X-ray (photon) having a constant energy is irradiated on a sample, photo-electrons are emitted from the sample. A measurement of kinetic energies of these photo-electrons can show how much binding energy is required to emit photo-electrons from the sample. Because this binding energy is one of intrinsic properties of atoms which emit photo-electrons, measuring the energy value may lead to an elemental analysis. Therefore, an analysis of a sample is performed by measuring the binding energy value of photo-electrons. A surface analysis was performed by XPS (Sigma Probe, Thermo-VG, UK) using a short-wavelength Al K$\alpha$ X-ray (1486.7 eV). A powder sample was pressed into a carbon tape and measured under vacuum conditions.

Figure 3:
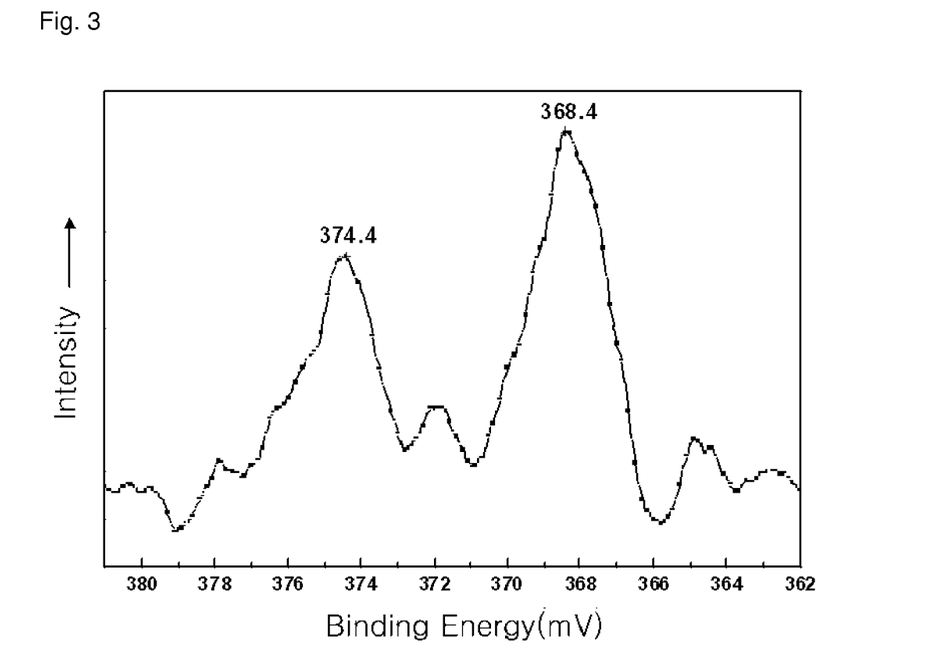
FIG. 3 is an XPS energy spectrum of Example 1 according to the present invention.
Figure 4:
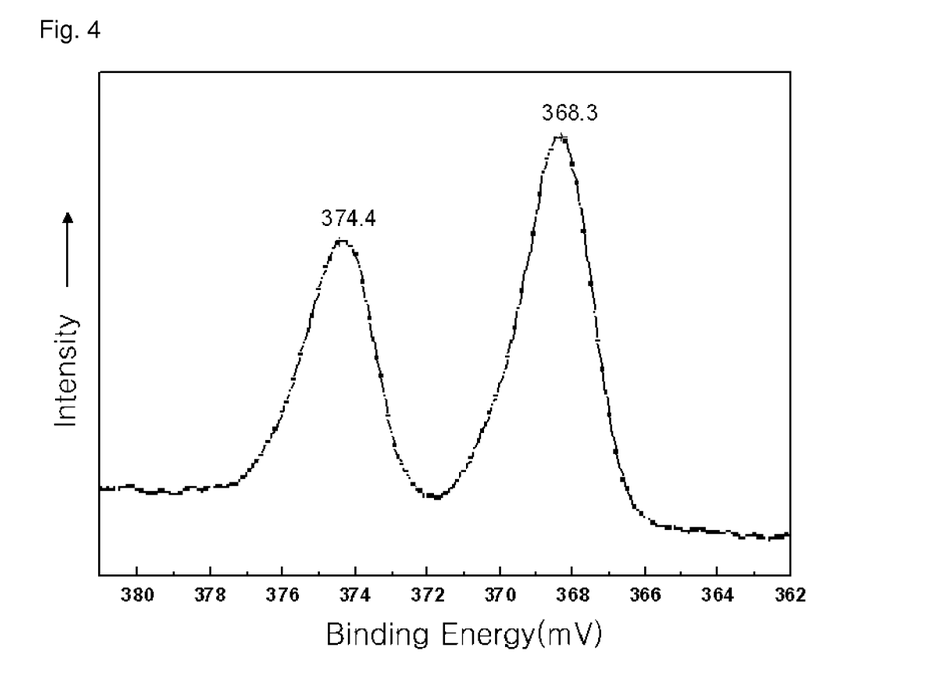
FIG. 4 is an XPS energy spectrum of Example 2 according to the present invention.
Figure 5:
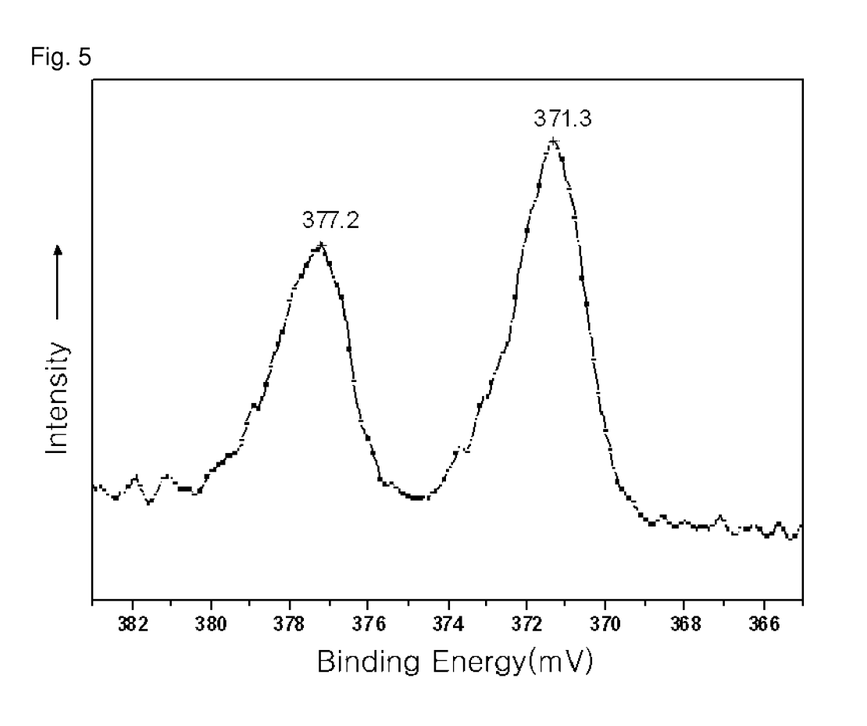
FIG. 5 is an XPS energy spectrum of Example 4 according to the present invention.

The results were illustrated in FIGS. 3 to 5. More specifically, XPS energy spectra in Examples 1, 2, and 4 are illustrated in FIGS. 3, 4, and 5, respectively.

As shown in FIG. 3, the presence of the $Ag^+$ species may be confirmed from $Ag\ 3d_{3/2}$ and $Ag3d_{5/2}$ peaks at 374.4 eV and 368.4 eV, respectively.

As shown in FIG. 4, the presence of the $Ag^{++}$ species may be confirmed from $Ag\ 3d_{3/2}$ and $Ag3d_{5/2}$ peaks at 374.4 eV and 368.3 eV, respectively.

As shown in FIG. 5, the presence of the $Ag^{+++}$ species may be confirmed from $Ag\ 3d_{3/2}$ and $Ag3d_{5/2}$ peaks at 377.2 eV and 371.3 eV, respectively.

From these results, it can be seen that silver in various oxidation states may be stabilized by forming a complex of silver with polydiguanide.

Experimental Example 3

Measurement of Number Average Particle Diameter and Zeta Potential of a Nanocrystalline Silver/Polydiguanide Complex To measure a number average particle diameter and zeta potential of a nanocrystalline silver/polydiguanide complex, the following experiments was performed.

Zeta potentials of a nanocrystalline complex synthesized when the water to surfactant molar ratio (R) is 8, 10, 12.4, and 15 (the concentration of the aqueous solution of silver nitrate is 5 mM) were measured using an electrophoretic light scattering spectrometer (ELS 8000, Otsuka Electronics, Osaka, Japan). For measurement, a powder sample in Example 4 was dispersed in 1 to 2 ml of DMSO. When the dispersed particles are too big, the solution was centrifuged for 1 minute to take the supernatant. 100 to 150 ml of an extra solvent was prepared for washing of the machine and dilution of the sample during the measurement of zeta potentials.

In the water to surfactant molar ratio (R), number average particle diameters and zeta potentials corresponding to various compositions and concentrations of silver nitrate given are summarized in the following Table 2.

The test organisms include 4 strains of Gram-negative bacteria: *Acinetobacter calcoaceticus* (ATCC 23055), *Citrobacter freundii* (ATCC 6750), *Klebsiella pneumonia* (ATCC 10031) and *Pseudomonas aeruginosa* (ATCC 27853); 4 strains of Gram-positive bacteria: *Enterococcus faecalis* (ATCC 29212), *Staphylococcus aureus* (ATCC 25923), *Staphylococcus epidermidis* (ATCC 12228), and *Propionibacterium acnes* (ATCC 6919). All challenge bacterial strains were obtained from American Type Culture Collection (ATCC, Rockville, Md., USA) except for *P. acnes* ATCC 6919 which was provided by Korean Collection for Type Cultures (Daejon, Korea). All tests were performed in line with Clinical and Laboratory Standards Institute (formerly National Committee for Clinical Laboratory Standard, NCCLS) guidelines. The overnight cultures served as the inocula for experiments. Unless otherwise stated, the strains were grown overnight in Tryptic Soy broth or agar (TSB or TSA, Difco Laboratories, Detroit, Mich., USA) at 37° C. under aerobic conditions. *P. acnes* (ATCC 6919) inocula were cultured in Brain Heart Infusion broth or agar (BHI, Difco Laboratories, Detroit, Mich., USA) supplemented with 1% glucose (BHIG). They were grown for 48 h at 37° C. under anaerobic conditions created by the GasPak jar system (BBL Microbiology Systems, Cockeysville, Md.).

TABLE 2

| Water to surfactant molar ratio (R) | Microemulsion composition (wt %) water/AOT/heptane | AOT/Heptane (wt %/wt %) | AOT/Water (wt %/wt%) | AgNO$_3$ (mM) | Number average particle diameter (nm) | zeta potential (mV) |
|---|---|---|---|---|---|---|
| 8 | 2.0/6.0/92.0 | 0.07 | 3.0 | 5.0 | 6.71 ± 1.10 | 44.29 ± 1.70 |
| 10 | 2.4/6.0/91.6 | | 2.5 | | 20.08 ± 6.11 | 65.01 ± 4.88 |
| 12.4 | 3.0/6.0/91.0 | | 2.0 | | 18.57 ± 2.92 | 66.11 ± 2.34 |
| 15 | 4.0/6.0/90.0 | | 1.5 | | 4.17 ± 1.04 | 68.77 ± 1.65 |

Referring to Table 2, it can be seen that nanocrystalline silver/polydiguanide complexes according to the present invention are monodispersed and their number average particle diameters are in the nanometer range. It can be also seen that zeta potentials of nanocrystalline silver/polydiguanide complexes according to the present invention are at least 0.

Also, in the water to surfactant molar ratio (R), number average particle diameters corresponding to various compositions and concentrations of silver nitrate given are summarized in the following Table 3.

TABLE 3

| Water to surfactant molar ratio (R) | Microemulsion composition (wt %) water/AOT/heptane | AOT/heptane (wt %/wt %) | AOT/water (wt %/wt %) | AgNO$_3$ (mM) | Number average particle diameter(?) |
|---|---|---|---|---|---|
| 15 | 4.0/6.0/90.0 | 0.07 | 1.5 | 10.0 | 21.20 ± 6.42 |
| | | | | 7.5 | 5.96 ± 2.79 |
| | | | | 5.0 | 4.17 ± 1.04 |
| | | | | 2.5 | 4.14 ± 0.96 |
| | | | | 1.0 | 3.95 ± 0.74 |

Referring to Table 3, it can be seen that nanocrystalline silver/polydiguanide complexes according to the present invention are monodispersed and their number average particle diameters are in the nanometer range.

From these results, it can be also seen that number average particle diameters and zeta potentials of a nanocrystalline silver/polydiguanide complex according to the present invention is in the nanometer range and at least 0, respectively.

Experimental Example 4

Evaluation of Antibacterial Performance

To evaluate an antibacterial performance of a silver/polydiguanide complex according to the present invention, the following experiment was performed.

Minimal inhibitory concentrations (MICs) of the antibacterial agents to inhibit the growth of bacteria in Examples 1 to 3 according to the present invention were determined by the agar dilution method in BHI agar for *P. acnes* or in Mueller Hinton agar (MH, Difco Laboratories, Detroit, Mich., USA) for all the other species, using a multi-point inoculator. Plates were read after incubation at 37° C. for 48 hours under anaerobic conditions (GasPak) for *P. acnes*, or for 24 hours in air for all the other species. To determine the MICs by the broth microdilution method, Mueller Hinton broth (MH, Difco Laboratories, Detroit, Mich., USA) was used for all bacterial strains except for *P. acnes* ATCC 6919, which was grown in BHI broth supplemented with 1% glucose. Strains were cultured in 96 well microplates. To evaluate the inhibitory effects of the antibacterial agents on bacterial growth, each well was supplemented with a range of concentrations of the active agents. Following 24 hours incubation in air or 48 hours incubation in GasPak jar system at 37° C., the wells were inspected for microbial growth and the MIC was determined as the lowest concentration that did not produce visual growth. The results by the agar dilution method are summarized in the following Table 4 and the results by the broth microdilution method were summarized in the following Table 5.

TABLE 4

Antibacterial activity by the agar dilution method (MIC, mg/L)

| Organisms | Gram Stain | Example 1 | Example 2 (values in μM) | Example 3 | Comparative Example 1 | AgSD[a] (values in μM) |
|---|---|---|---|---|---|---|
| *Acinetobacter calcoaceticus* | G− | 1 | 1 (1.5) | 1 | 4 | 4-16 (11-45) |
| *Citrobacter freundii* | G− | 8 | 4-8 (6-12) | 8-16 | 32 | — |
| *Enterococcus faecalis* | G+ | 8 | 4-8 (6-12) | 4-8 | 32 | 4-64 (11-179) |
| *Klebsiella pneumoniae* | G− | 2-4 | 2-4 (3-6) | 2-4 | 32 | 32-64 (90-179) |
| *Pseudomonas aeruginosa* | G− | 8 | 16 (24) | 16 | 32-64 | 16-32 (45-90) |
| *Staphylococcus epidermidis* | G+ | 1 | 1 (1.5) | 1 | 8 | 8-16 (22-90) |
| *Staphylococcus aureus* | G+ | 2 | 2 (3) | 2 | 16 | 32-128 (90-358) |
| *Propionibacteriumacne* | G+ | — | 0.25 (0.38) | 0.25 | 2 | — |

[a]silver sulfadiazine

TABLE 5

Antibacterial activity by the broth microdilution method (MIC, mg/L)

| Organisms | Gram Strain | Example 1 | Example 2 (values in μM) | Example 3 | Comparative Example 1 | AgSD[a] (values in μM) |
|---|---|---|---|---|---|---|
| *Acinetobacter calcoaceticus* | G− | 0.25-0.5 | 0.12-0.25 (0.18-0.38) | 0.12-2.5 | 2 | — |
| *Citrobacter freundii* | G− | 1 | 2-4 (3-6) | 8 | 8-16 | 6.25-50 (17.5-140) |
| *Enterococcus faecalis* | G+ | 4-8 | 1-2 (1.5-3) | 1-2 | 8-16 | 50-100 (140-280) |
| *Klebsiella pneumoniae* | G− | 1 | 0.5 (0.75) | 0.5 | 8 | 12.5-100 (35-280) |
| *Pseudomonas aeruginosa* | G− | 4 | 4 (6) | 4 | 8-16 | 6.25-50 (17.5-140) |
| *Staphylococcus epidermidis* | G+ | 0.5 | 0.12-0.25 (0.18-0.38) | 0.12-0.25 | 2-4 | 6.25-50 (17.5-140) |
| *Staphylococcus aureus* | G+ | 1 | 0.5 (0.75) | 0.5 | 4-8 | 25-100 (70-280) |
| *Propionibacteriumacne* | G+ | — | 0.06 (0.09) | 0.06 | 1 | — |

[a]silver sulfadiazine

Values in parenthesis of the Example 2 and AgSD column in Tables 4 and 5 indicate the MICs expressed as μmole/L.

Referring to Tables 4 and 5, it can be seen that samples in Examples 1 to 3 exhibit lower MICs than that in Comparative Example 1, and have much lower MICs by 10 to 100 folds or more compared to silver sulfadiazine which is a conventional agent for burns treatment.

From these results, it can be seen that a silver/polydiguanide complex according to the present invention has a low MIC value, exhibiting a very good antibacterial activity.

Therefore, a silver/polydiguanide complex according to the present invention is different from conventional silver/polydiguanide complexes in carbon, hydrogen, and nitrogen contents as well as in structure of silver and polydiguanide, and solubility, is a material that exhibits a very good antibacterial activity due to a much lower minimal inhibitory concentration (MIC) value by 10 to 100 folds or more compared to silver sulfadiazine which is a conventional therapeutic agent for burns, and may be usefully used as an antibacterial composition for burns or wounds treatment.

The invention claimed is:

1. A nanocrystalline silver/polydiguanide complex comprising silver and polydiguanide, wherein the silver and the polydiguanide forms the nanocrystalline silver/polydiguanide complex, which is stabilized in an oxidation state of an integer of 1 to 4, a mole ratio between the silver and the polydiguanide is 1:1-4, an average particle diameter of the nanocrystalline silver/polydiguanide complex is ranging from 1 nm to 200 nm, and a zeta potential of the nanocrystalline silver/polydiguanide complex greater than or equal to zero.

2. The complex according to claim 1, wherein the mole ratio between the silver and the polydiguanide is 1:1-2.

3. A nanocrystalline silver/polydiguanide complex of claim 1, wherein the polydiguanide comprises at least two biguanide moieties.

4. A nanocrystalline silver/polydiguanide complex of claim 1, wherein the polydiguanide is selected from the group consisting a poly(hexamethylenebiguanide), a 1,1'-hexamethylenebis[5-(p-chlorphenyl)biguanide], a N'—,N'-dimethylbiguanide, a phenethylbiguanide, and a N-butylbiguanide.

5. An antibacterial composition for burns or wounds treatment comprising a nanocrystalline silver/polydiguanide complex of claim 1 as an active ingredient.

6. A nanocrystalline silver/polydiguanide complex according to claim 1, wherein the nanoparticle is prepared by the process comprising:
preparing a water-in-oil microemulsion;
adding an aqueous solution of polydiguanide into the water-in-oil microemulsion to prepare a resultant solution;

adding an aqueous solution containing silver (I) into the resultant solution to prepare a reaction mixture; and precipitating a nanocrystalline silver/polydiguanide complex by adjusting the pH of the reaction mixture, wherein the nanocrystalline silver/polydiguanide complex comprises nanocrystalline silver (I)/polydiguanide complex.

7. A nanocrystalline silver/polydiguanide complex according to claim 1, wherein the nanocrystalline silver/polydiguanide complex is prepared by the process comprising:

preparing a water-in-oil microemulsion;

adding an aqueous solution of polydiguanide into the water-in-oil microemulsion to prepare a resultant solution;

adding an aqueous solution containing silver (I) into the resultant solution to prepare a reaction mixture;

oxidizing the silver (I) in the reaction mixture to a high valent silver selected from the group consisting of silver (II), silver (III), silver (IV), and a combination thereof by adding an oxidizing agent into the reaction mixture; and precipitating the nanocrystalline silver/polydiguanide complex by adjusting the pH of the reaction mixture, wherein the nanocrystalline silver/polydiguanide complex comprises one selected from the group consisting of a nanocrystalline silver (II)/polydiguanide complex, a nanocrystalline silver (III)/polydiguanide complex, a nanocrystalline silver (IV)/polydiguanide complex, and a combination thereof.

8. A method for preparing a nanocrystalline silver/polydiguanide complex, comprising:

step 1 of preparing a water-in-oil microemulsion;

step 2 of adding an aqueous solution of polydiguanide into the water-in-oil microemulsion prepared in step 1 to prepare a resultant solution;

step 3 of adding an aqueous solution containing silver (I) into the resultant solution in step 2 to prepare a reaction mixture; and step 4 of precipitating the nanocrystalline silver/polydiguanide complex by adjusting the pH of the reaction mixture in step 3, wherein the nanocrystalline silver/polydiguanide complex comprises nanocrystalline silver (I)/polydiguanide complex, wherein a mole ratio between the silver and the polydiguanide is 1:1-4, an average particle diameter of the nanocrystalline silver/polydiguanide complex ranged from 1 nm to 200 nm, and a zeta potential of the nanocrystalline silver/polydiguanide complex is greater than or equal to zero.

9. The method according to claim 8, wherein the water-in-oil microemulsion in step 1 comprises an organic solvent and a surfactant selected from the group consisting of a cationic surfactant, an anionic surfactant, a zwiterionic surfactant, and a non-ionic surfactant.

10. The method according to claim 8, wherein the water-in-oil microemulsion in step 1 further comprises a co-surfactant which is selected from the group consisting of a cationic surfactant, an anionic surfactant, a zwiterionic surfactant and a non-ionic surfactant.

11. The method according to claim 8, wherein the aqueous solution of polydiguanide in step 2 is prepared by adjusting the pH to a range of 0 to 3.

12. The method according to claim 8, wherein the pH in step 4 is adjusted to a range of 3 to 8.

13. A method for preparing a nanocrystalline silver/polydiguanide complex, comprising:

step 1 of preparing a water-in-oil microemulsion;

step 2 of adding an aqueous solution of polydiguanide into the water-in-oil microemulsion prepared in step 1 to prepare a resultant solution;

step 3 of adding an aqueous solution containing silver (I) into the resultant solution in step 2 to prepare a reaction mixture;

step 4 of oxidizing the silver (I) to a high valent silver selected from the group consisting of silver (II), silver (III), silver (IV), and a combination thereof, by adding an oxidizing agent into the reaction mixture obtained in step 3; and step 5 of precipitating the nanocrystalline silver/polydiguanide complex by adjusting the pH of the reaction mixture in step 4, wherein the nanocrystalline silver/polydiguanide complex comprises one selected from the group consisting of a nanocrystalline silver (II)/polydiguanide complex, a nanocrystalline silver (III)/polydiguanide complex, a nanocrystalline silver (IV)/polydiguanide complex, and a combination thereof, wherein a mole ratio between the silver and the polydiguanide is 1:1-4, an average particle diameter of the nanocrystalline silver/polydiguanide complex ranging from 1 nm to 200 nm, and a zeta potential of the nanocrystalline silver/polydiguanide complex is greater than or equal to zero.

14. The method according to claim 13, wherein the water-in-oil microemulsion in step 1 comprises an organic solvent and a surfactant selected from the group consisting of a cationic surfactant, an anionic surfactant, a zwiterionic surfactant, and a non-ionic surfactant.

15. The method as according to claim 13, wherein the water-in-oil microemulsion in step 1 further comprises a co-surfactant which is selected from the group consisting of a cationic surfactant, an anionic surfactant, a zwiterionic surfactant and a non-ionic surfactant.

16. The method according to claim 13, wherein the aqueous solution of polydiguanide in step 2 is prepared by adjusting the pH to a range of 0 to 3.

17. The method according to claim 13, wherein the oxidizing agent in step 4 is selected from a group consisting of sodium peroxydisulfate, potassium peroxydisulfate, ammonium peroxydisulfate, red lead, and combinations thereof.

18. The method according to claim 13, wherein the oxidation in step 3 is performed by adding the oxidizing agent at a predetermined condition, wherein a pH value is ranged from 1 to 5, temperature is ranged from 0° C. to 80° C., and reacting time is ranged from 30 seconds to 8 hours.

19. The method according to claim 13, wherein the pH in step 5 is adjusted to a range of 3 to 8.

* * * * *